(12) United States Patent
McGlinch et al.

(10) Patent No.: US 7,625,365 B2
(45) Date of Patent: *Dec. 1, 2009

(54) INTRAVASCULAR DEVICE AND CARRIER TUBE WITH INTERFERENCE FIT MEMBER

(75) Inventors: Timothy McGlinch, St. Paul, MN (US); Ajay Gupta, Little Canada, MN (US); Albert S. Benjamin, Maplewood, MN (US); August L. Powell, Zimmerman, MN (US); John E. Uschold, North Branch, MN (US); Tim Mlsna, St. Michael, MN (US); Dean A. Peterson, Brooklyn Park, MN (US); David B. Robinson, Chanhassen, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 951 days.

This patent is subject to a terminal disclaimer.

(21) Appl. No.: 10/244,870

(22) Filed: Sep. 17, 2002

(65) Prior Publication Data

US 2003/0125713 A1 Jul. 3, 2003

Related U.S. Application Data

(63) Continuation-in-part of application No. 09/960,260, filed on Sep. 21, 2001, now Pat. No. 7,214,220.

(60) Provisional application No. 60/360,614, filed on Feb. 28, 2002.

(51) Int. Cl.
A61M 25/16 (2006.01)

(52) U.S. Cl. .................. 604/533; 206/571

(58) Field of Classification Search .......... 604/96.01, 604/103.03, 103.04, 158, 161, 162, 246, 604/256, 264, 164.08, 523–539, 284, 915, 604/921, 163, 171; 206/571, 438; 606/191, 606/194

See application file for complete search history.

(56) References Cited

U.S. PATENT DOCUMENTS

| 2,185,741 | A | | 1/1940 | Sorg et al. |
| RE25,788 | E | | 6/1965 | Sheridan |
| 3,318,335 | A | | 5/1967 | Heller |
| 3,348,544 | A | | 10/1967 | Braun |
| 3,470,869 | A | | 10/1969 | Fenton et al. |
| 3,720,210 | A | * | 3/1973 | Diettrich .............. 604/533 |
| 3,725,522 | A | | 4/1973 | Sheridan et al. |
| 3,752,510 | A | | 8/1973 | Windischman et al. |

(Continued)

FOREIGN PATENT DOCUMENTS

EP 0 782 868 A1 7/1997

(Continued)

*Primary Examiner*—Nicholas D Lucchesi
*Assistant Examiner*—Theodore J Stigell
(74) *Attorney, Agent, or Firm*—Crompton, Seager & Tufte, LLC

(57) ABSTRACT

An intravascular device can have an elongate shaft and a proximal hub assembly. The proximal hub assembly can include an interference fit member (IFM) which forms an interference fit with a carrier tube to reduce the tendency of the device to fall out of the carrier tube during handling and to provide for easy removal of the device when ready for use.

19 Claims, 19 Drawing Sheets

U.S. PATENT DOCUMENTS

| | | | |
|---|---|---|---|
| 3,809,081 A * | 5/1974 | Loveless | 604/170.02 |
| 3,861,972 A | 1/1975 | Glover et al. | |
| 3,865,666 A | 2/1975 | Shoney | |
| 3,873,391 A | 3/1975 | Plauka et al. | |
| 3,914,002 A | 10/1975 | Berliner et al. | |
| 3,950,052 A | 4/1976 | Walter et al. | |
| 3,959,429 A | 5/1976 | Benning | |
| 3,985,601 A | 10/1976 | Panagrossi | |
| 3,989,571 A | 11/1976 | Harautuneian | |
| 4,068,659 A * | 1/1978 | Moorehead | 604/508 |
| 4,085,185 A | 4/1978 | Adair | |
| 4,093,484 A | 6/1978 | Harrison et al. | |
| 4,154,244 A | 5/1979 | Becker et al. | |
| 4,171,943 A | 10/1979 | Tschanz et al. | |
| 4,191,185 A | 3/1980 | Lemieux | |
| 4,198,983 A | 4/1980 | Becker et al. | |
| 4,207,900 A | 6/1980 | Patel et al. | |
| 4,210,478 A | 7/1980 | Shoney | |
| 4,284,459 A | 8/1981 | Patel et al. | |
| 4,328,056 A | 5/1982 | Snooks | |
| 4,354,495 A | 10/1982 | Bodicky | |
| 4,417,887 A * | 11/1983 | Koshi | 604/162 |
| 4,489,961 A | 12/1984 | Laidig | |
| 4,509,877 A | 4/1985 | Sobin et al. | |
| 4,511,163 A | 4/1985 | Harris et al. | |
| 4,607,746 A | 8/1986 | Stinnette | |
| 4,880,414 A | 11/1989 | Whipple | |
| 4,960,412 A * | 10/1990 | Fink | 604/167.04 |
| 5,031,775 A | 7/1991 | Kane | |
| 5,059,174 A * | 10/1991 | Vaillancourt | 604/82 |
| 5,217,114 A * | 6/1993 | Gadberry et al. | 206/364 |
| 5,224,939 A * | 7/1993 | Holman et al. | 604/528 |
| 5,344,011 A | 9/1994 | DiBernardo et al. | |
| 5,366,444 A | 11/1994 | Martin | |
| 5,380,301 A * | 1/1995 | Prichard et al. | 604/533 |
| 5,524,757 A * | 6/1996 | Andrews et al. | 206/438 |
| 5,607,055 A | 3/1997 | Bettinger | |
| 5,810,867 A | 9/1998 | Zarbatany et al. | |
| 5,830,401 A | 11/1998 | Prichard et al. | |
| 5,843,048 A * | 12/1998 | Gross | 604/264 |
| 5,891,110 A * | 4/1999 | Larson et al. | 604/523 |
| 6,053,313 A | 4/2000 | Farrell et al. | |
| 6,068,121 A | 5/2000 | McGlinch | |
| 6,068,622 A | 5/2000 | Sater et al. | |
| 6,113,576 A * | 9/2000 | Dance et al. | 604/164.01 |
| 6,228,073 B1 | 5/2001 | Noone et al. | |
| 6,273,404 B1 | 8/2001 | Holman et al. | |
| 6,398,031 B1 * | 6/2002 | Frezza | 206/571 |
| 6,491,681 B1 * | 12/2002 | Kunis et al. | 604/528 |
| 6,503,244 B2 * | 1/2003 | Hayman | 604/525 |
| 6,575,959 B1 * | 6/2003 | Sarge et al. | 604/533 |
| 7,214,220 B2 * | 5/2007 | McGlinch et al. | 604/533 |

FOREIGN PATENT DOCUMENTS

| | | |
|---|---|---|
| FR | 2.092.970 | 1/1972 |
| WO | WO 98/18515 | 5/1998 |

\* cited by examiner

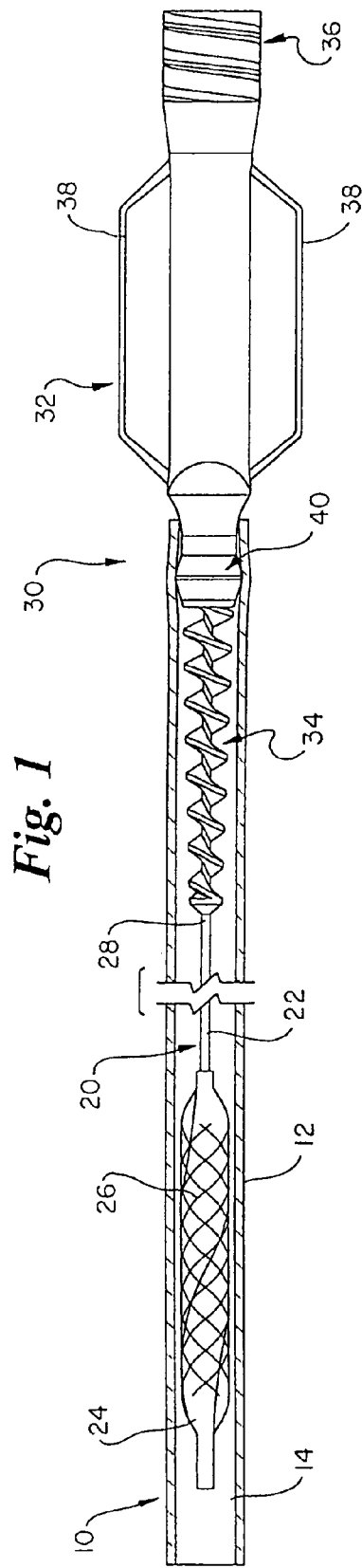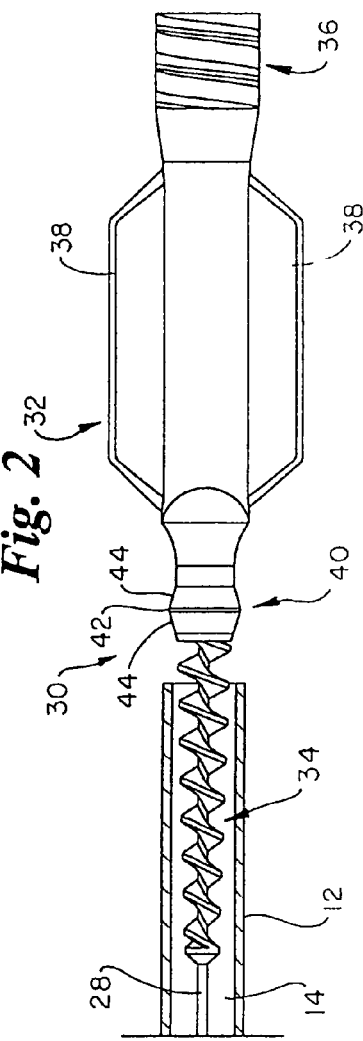

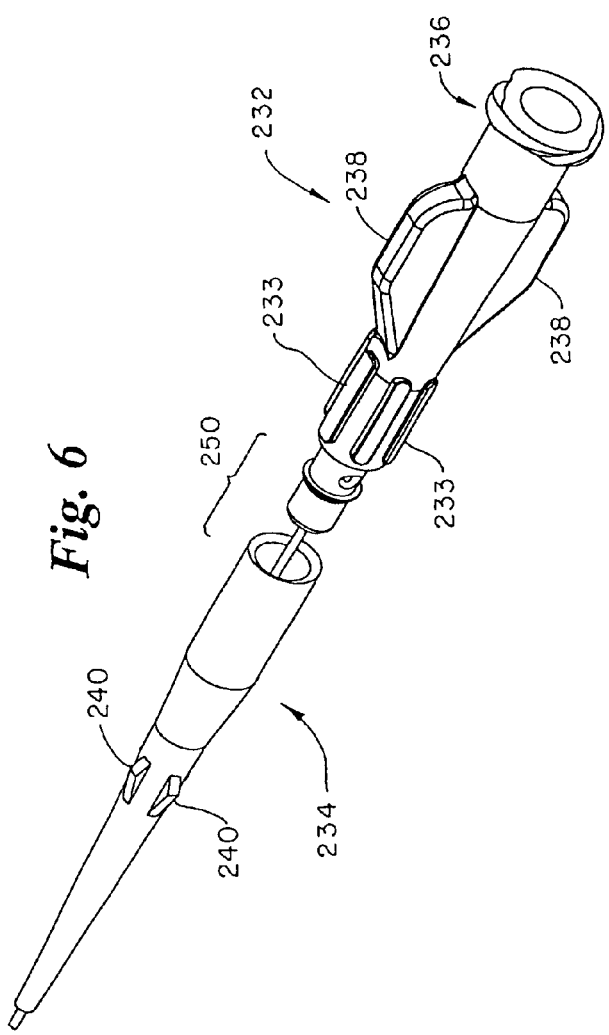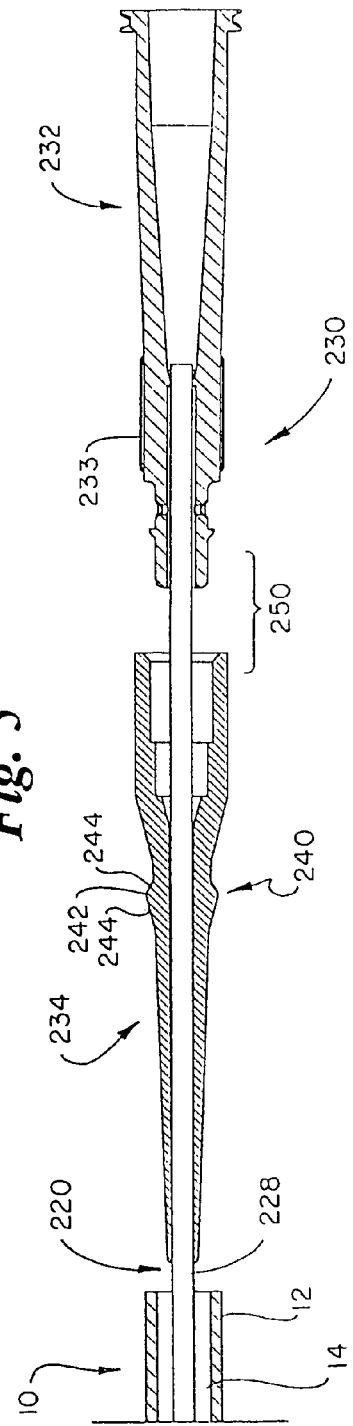

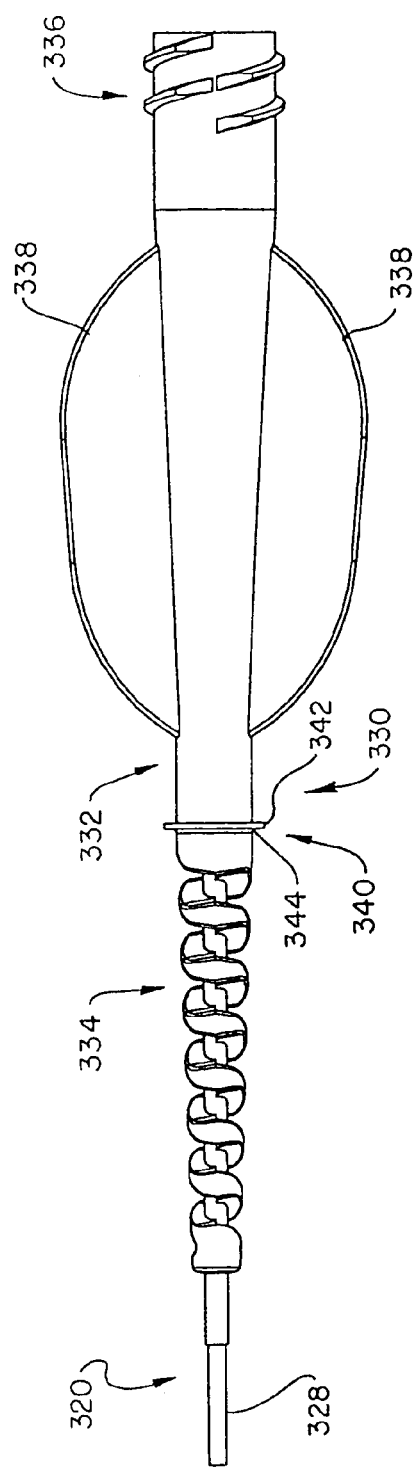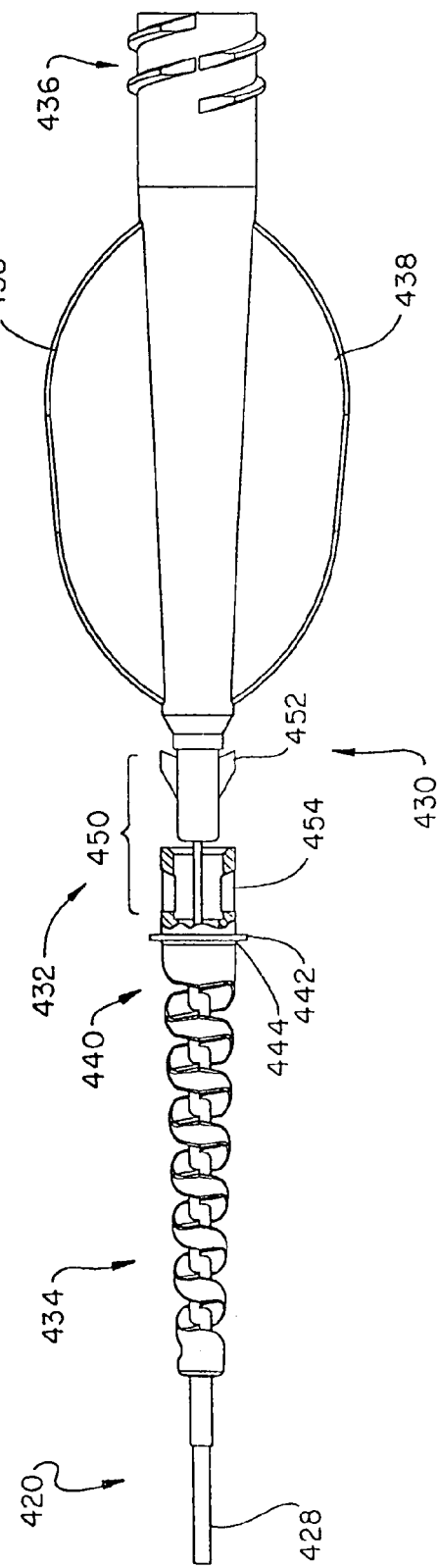

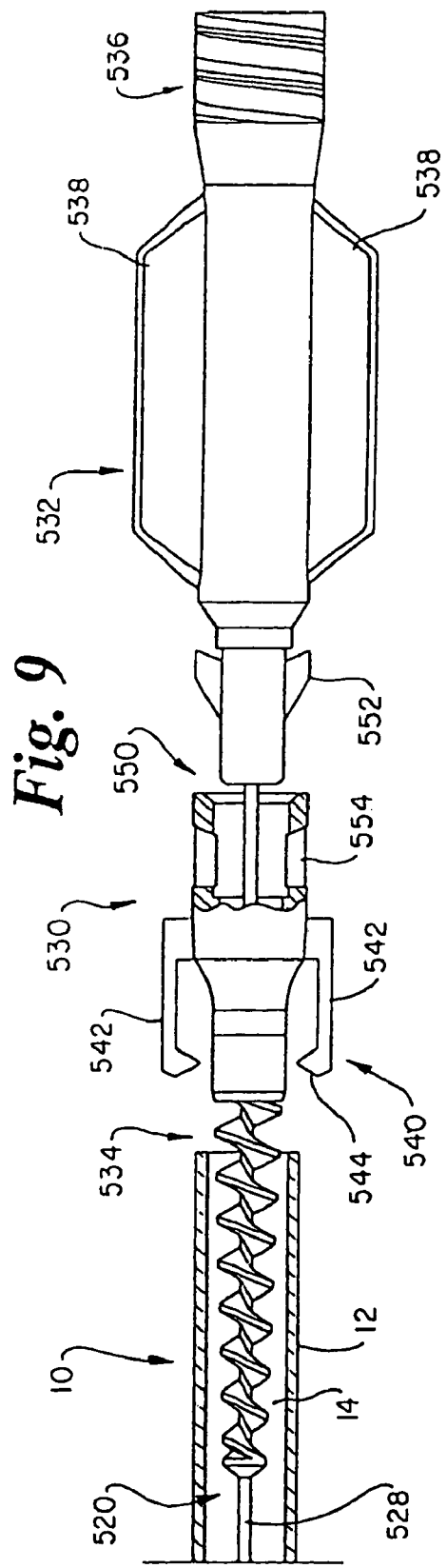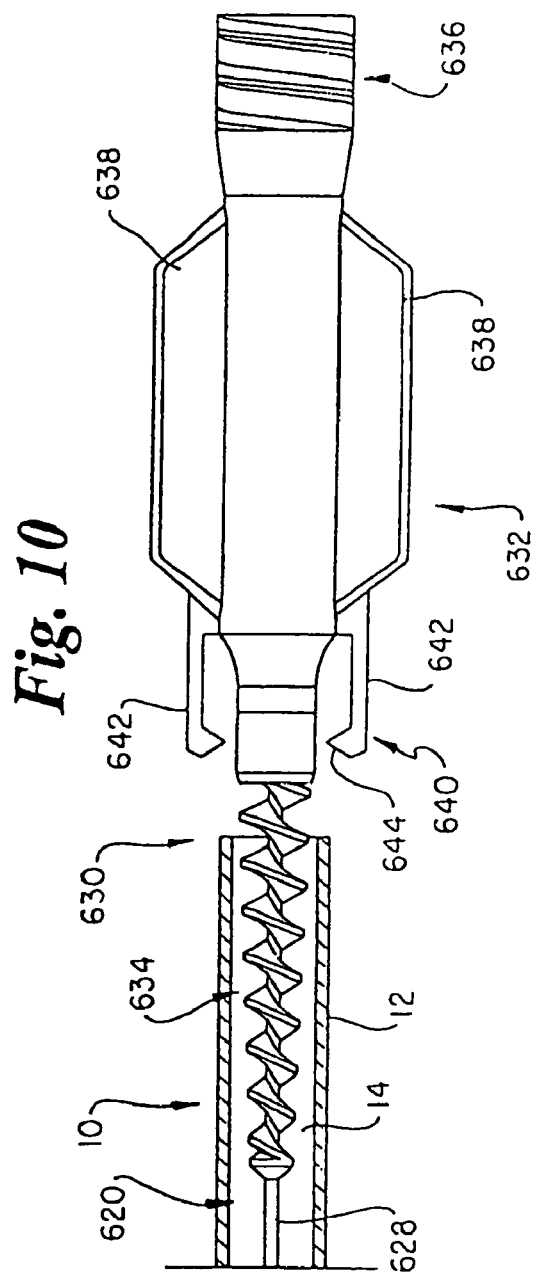

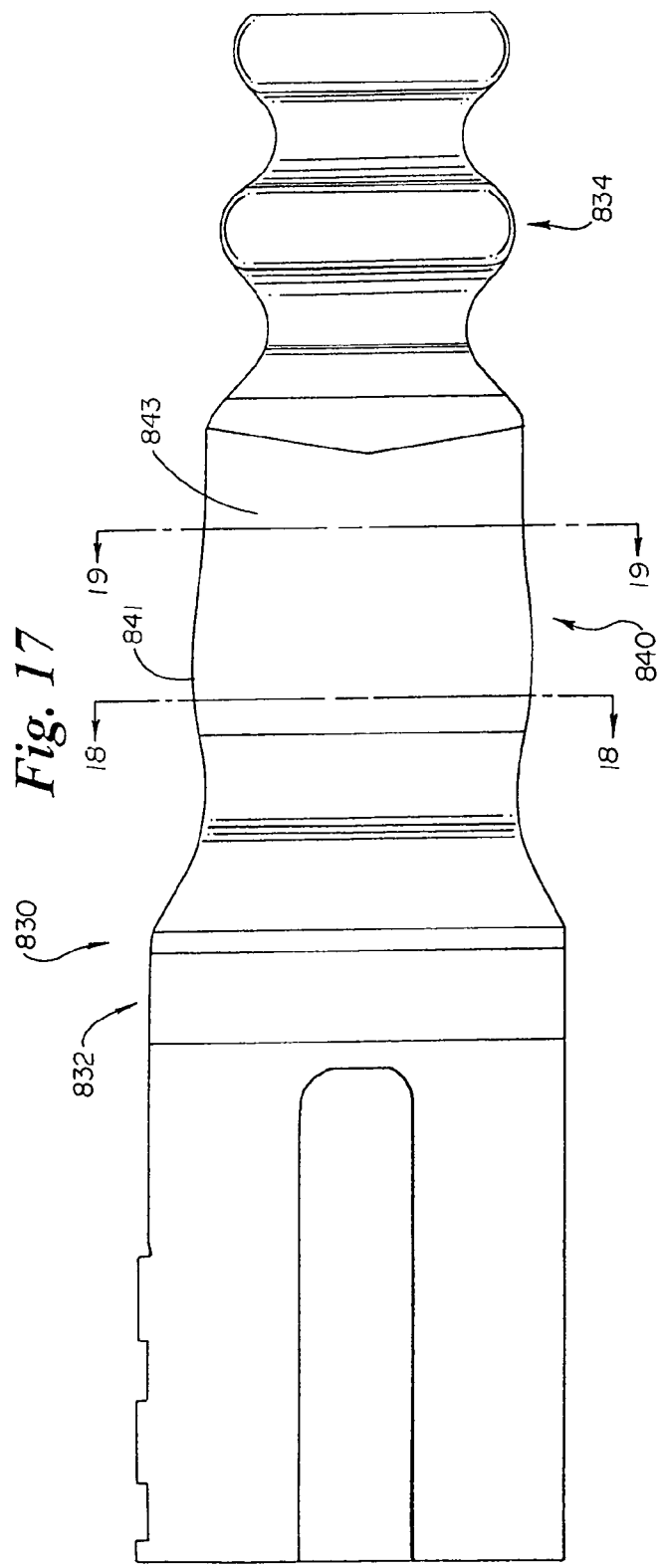
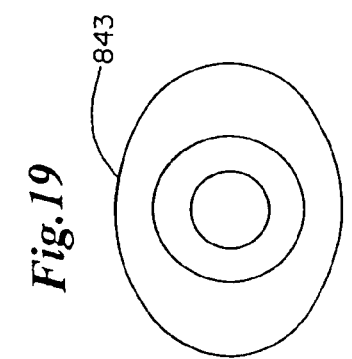
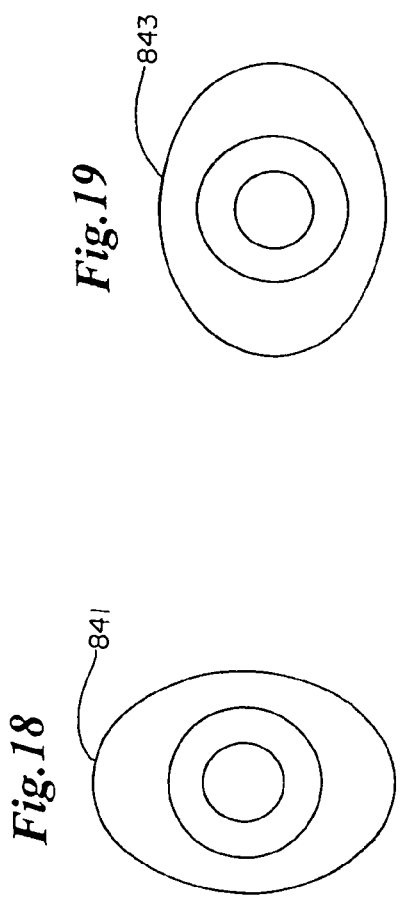

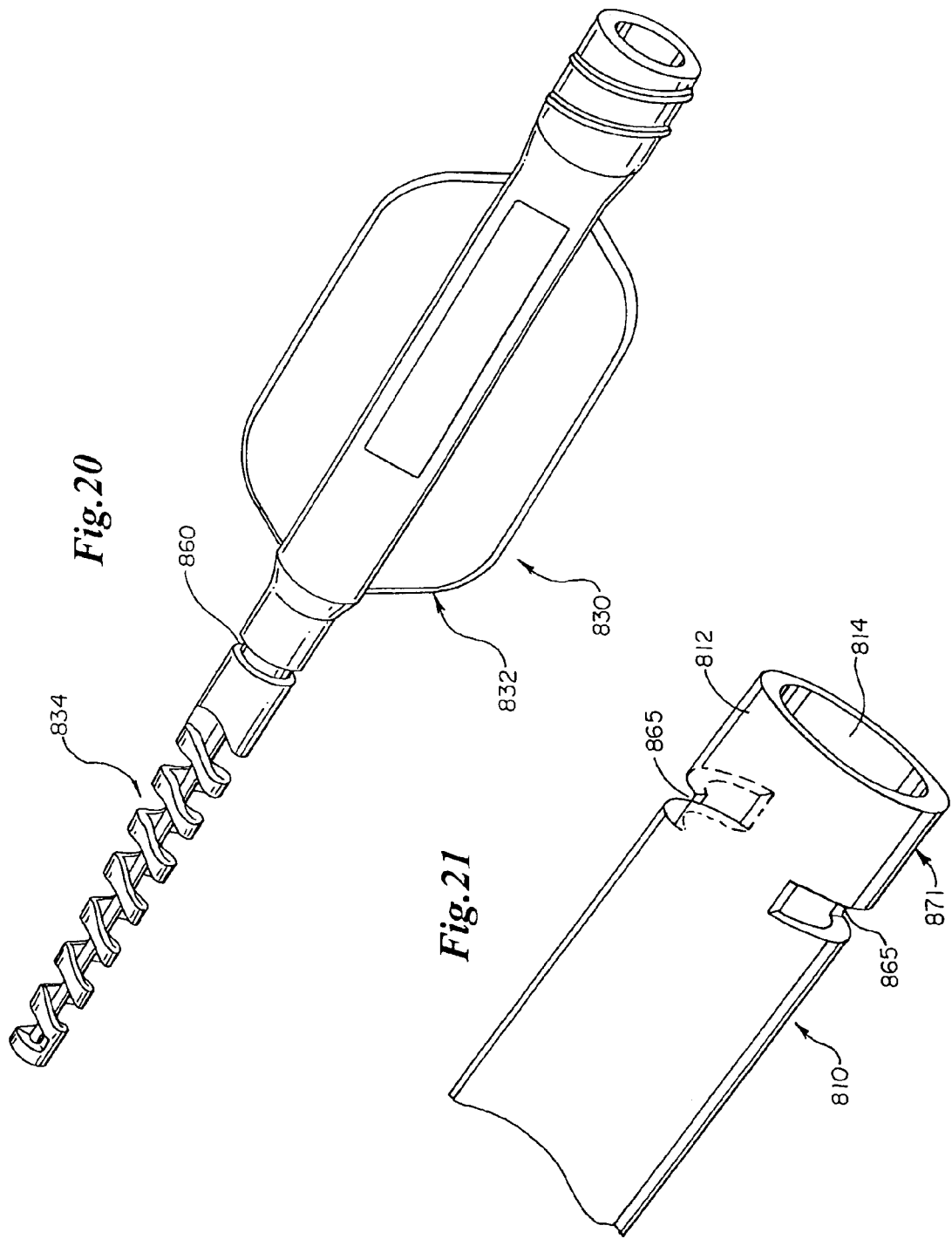

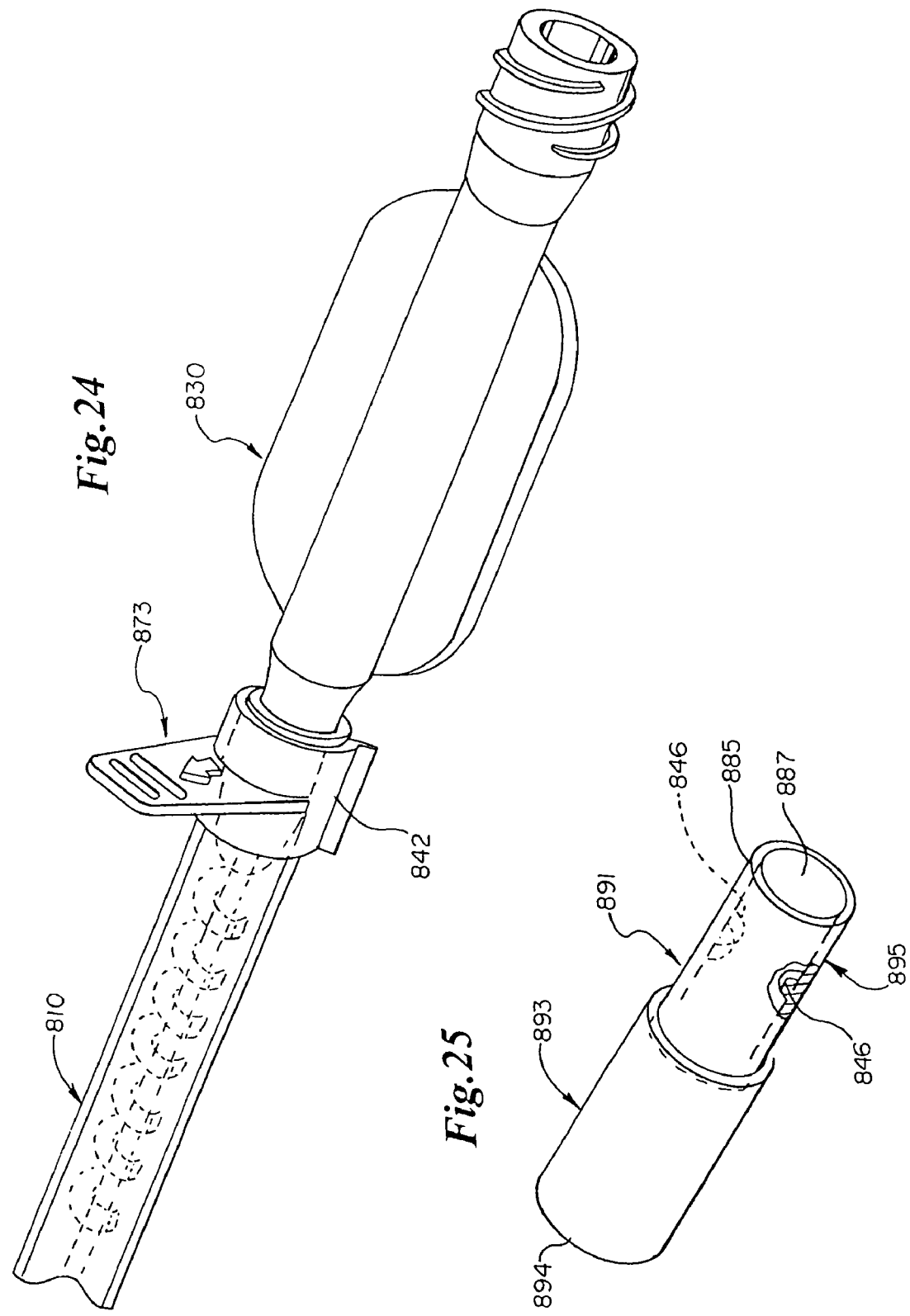

INTRAVASCULAR DEVICE AND CARRIER TUBE WITH INTERFERENCE FIT MEMBER

RELATED APPLICATIONS

This application claims priority to provisional application 60/360,614, filed Feb. 28, 2002 entitled "MANIFOLD SECUREMENT IN CARRIER TUBE". This application is also a continuation-in-part of 09/960,260 filed Sep. 21, 2001, now U.S. Pat. No. 7,214,220, entitled "INTRAVASCULAR DEVICE WITH CARRIER TUBE ENGAGEMENT MEMBER". Both applications are explicitly incorporated by reference herein.

TECHNICAL FIELD

The invention relates to medical devices and packaging thereof.

BACKGROUND

Elongate intravascular devices can be packaged in carrier tubes. A carrier tube provides a way to package and handle an intravascular device, but the intravascular device can have a tendency to fall out of the carrier tube. As such, there is an ongoing need to provide improved devices and packaging techniques to reduce this tendency.

SUMMARY

The present invention provides a number of alternative solutions. One embodiment, for example, provides an intravascular device having an elongate shaft and a proximal hub assembly. The proximal hub assembly can include an interference fit member (IFM) that forms an interference fit with a carrier tube. The interference fit can reduce the tendency of the device to fall out of the carrier tube during shipping and handling, but can permit easy removal of the device when desired. In other embodiments, a manifold can include structure adapted and configured to mate with the carrier tube and/or a separate structure to maintain the carrier tube or other packaging structure in place.

Accordingly, an embodiment of the present invention can be found in an intravascular device that is suitable for packaging in a package lumen defined by a package lumen wall. The intravascular device includes an elongate shaft that has a proximal portion, a hub assembly that is connected to the proximal portion of the elongate shaft, and an interference fit member (IFM) that is positioned proximate the hub assembly. The IFM is adapted and configured to form an interference fit with the package lumen wall when the intravascular device is disposed in the package lumen.

Another embodiment of the present invention is found in a hub assembly for an intravascular device that is suitable for packaging in a carrier tube. The hub assembly includes an interference fit member (IFM) that is configured to form an interference fit with the carrier tube.

An embodiment of the present invention can be found in an intravascular device that is suitable for packaging in a package lumen defined by a package wall. The intravascular device includes an elongate shaft that has a proximal portion and a hub assembly that is connected to the proximal portion of the elongate shaft. The hub assembly includes means for forming an interference fit with the package wall when the intravascular device is disposed in the package lumen.

Another embodiment of the present invention can be found in a packaged intravascular device that includes a package that has a package lumen defined by a package wall and an intravascular device that is disposed in the package lumen. The intravascular device includes an elongate shaft that has a proximal portion and a hub assembly connected to the proximal portion of the elongate shaft, where the hub assembly includes means for forming an interference fit with the package wall.

An embodiment of the present invention can be found in an intravascular device that is suitable for packaging in a package lumen defined by a package lumen wall. The intravascular device includes an elongate shaft having a proximal portion and an interference fit member (IFM) connected to the proximal portion of the elongate shaft. The IFM is configured to form an interference fit with the package lumen wall when the intravascular device is disposed in the package lumen.

BRIEF DESCRIPTION OF THE DRAWINGS

FIG. 1 is a partially cross-sectioned plan view of a catheter disposed in a carrier tube. The catheter includes a hub assembly with a hub and an integral strain relief. An IFM is disposed on the hub and engages an inside surface of the carrier tube.

FIG. 2 is a partially cross-sectioned plan view of a proximal portion of the carrier tube and the catheter illustrated in FIG. 1, showing the IFM disengaged from the carrier tube.

FIG. 5 is a cross-sectioned exploded plan view of a proximal portion of a carrier tube and an alternative catheter. The catheter includes a hub assembly with a hub and a snap-fit strain relief, with an IFM disposed on the strain relief.

FIG. 6 is an exploded isometric view of the hub assembly illustrated in FIG. 5.

FIG. 7 is a plan view of a proximal portion of an alternative catheter that includes a hub assembly having a hub and an integral strain relief, with an IFM disposed on the hub.

FIG. 8 is a plan view of a proximal portion of an alternative catheter having a hub assembly with a hub and a snap-fit strain relief, with an IFM disposed on the strain relief.

FIG. 9 is an exploded view of a proximal portion of a carrier tube and an alternative catheter. The catheter includes a hub assembly having a hub and a snap-fit strain relief, with an IFM disposed on the strain relief, showing the IFM disengaged from the outside surface of the carrier tube.

FIG. 10 is a plan view of a proximal portion of a carrier tube and an alternative catheter. The catheter includes a hub assembly having a hub and an integral strain relief, with an IFM disposed on the hub, showing the IFM disengaged from the outside surface of the carrier tube.

FIG. 17 is a partial side view of another hub assembly.

FIG. 18 is a cross-sectional view taken along the line 18-18 of FIG. 17.

FIG. 19 is a cross-sectional view taken along the line 19-19 of FIG. 17.

FIG. 20 is a perspective view of a hub assembly having a single groove.

FIG. 21 is a perspective view of a carrier tube adapted to cooperate with the hub assembly of FIG. 20.

FIG. 24 is a perspective view of the hub assembly of FIG. 20, the carrier tube of FIG. 21 and the interference structure of FIG. 22 in cooperating position therebetween.

FIG. 25 is a perspective view of a connector structure.

DETAILED DESCRIPTION

Figure 3:
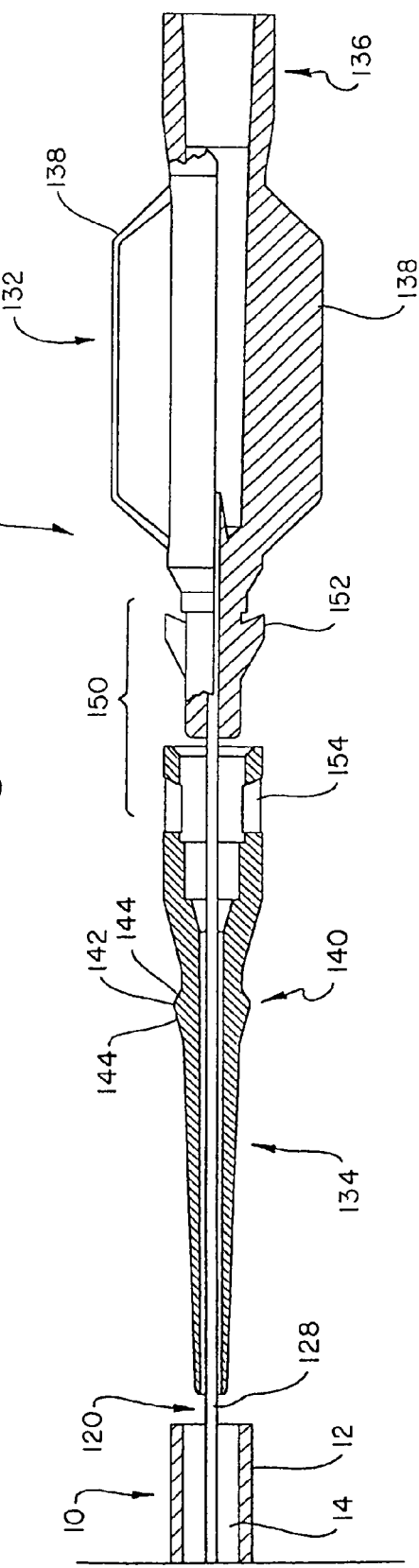
FIG. 3 is a partially cross-sectioned exploded plan view of a proximal portion of a carrier tube and an alternative catheter. The catheter includes a hub assembly with a hub and a snap-fit strain relief, with an IFM disposed on the strain relief.

The following detailed description should be read with reference to the drawings in which similar elements in different drawings are numbered the same. The drawings, which are not necessarily to scale, depict illustrative embodiments and are not intended to limit the scope of the invention.

FIG. 1 illustrates a partially cross-sectioned plan view of a package and an intravascular device disposed therein. By way of example, not limitation, the package 10 is shown to be a carrier tube 10 having a carrier tube lumen 14 defined by a carrier tube wall 12. The carrier tube lumen 14 can be sized to accommodate substantially the entire length of the intravascular device 20 therein. The carrier tube lumen 14 can have an open proximal end and an open or closed distal end.

The carrier tube 10 can be formed utilizing conventional materials, dimensions and techniques. For example, the carrier tube 10 can be formed of an extruded polymer including a blend of 50% polyolefin copolymer available under the trade name SURLYN and 50% high density polyethylene, having an inside diameter ranging from about 0.10 to about 0.30 inches (about 2.5 to about 7.6 millimeters), a wall thickness ranging from about 0.002 to about 0.020 inches (about 0.05 to about 0.5 millimeters), and a length ranging from about 12 to about 72 inches (about 30 to 180 centimeters). Other suitable polymers for the carrier tube 10 include thermoplastics such as fluoropolymers (PTFE, FEP, PFA, CTFE), nylons, phenylene oxides, polyesters, polyethylenes, polypropylene, polyurethanes and combinations thereof.

The intravascular device 20 can be removably disposed in the lumen 14 of the carrier tube 10. The intravascular device 20 generically refers to a wide variety of elongate intravascular devices such as catheters and guide wires. For example, the intravascular device 20 can include a balloon catheter, a guide catheter, a diagnostic catheter, a guide wire, a drug delivery catheter, an atherectomy catheter, a tubular sheath or a stent delivery catheter.

For purposes of illustration only, intravascular device 20 is shown in the form of an intravascular balloon catheter 20 having an elongate shaft 22, a distally mounted balloon 24 and a stent 26 disposed thereon. A proximal portion 28 of the elongate shaft 22 is connected to a hub assembly 30.

The hub assembly 30 includes a hub portion 32 and a strain relief 34. The proximal portion 28 of the elongate shaft 22 extends through the strain relief 34 and into the hub portion 32. The hub assembly 30 can be adhesively or thermally bonded to the proximal shaft portion 28. Alternatively, the proximal portion 28 of the elongate shaft 22 can be connected to the hub assembly 30 by an insert molding technique. As a further alternative, the hub assembly 30 can be removably connected to the proximal shaft portion 28 utilizing a releasable compression fitting.

The hub portion 32 and the strain relief 34 can be a two-piece construction or a one-piece construction as shown. Examples of one-piece and two-piece constructions are described in U.S. Pat. No. 6,273,404 B1 to Holman et al, the entire disclosure of which is incorporated herein by reference. In one-piece constructions, the hub portion 32 and the strain relief 34 can be formed of the same material, such as polycarbonate. Other moldable polymeric material having sufficient impact resistance and chemical resistance can be utilized as well. In two-piece constructions, the hub portion 32 and the strain relief 34 can be formed of two different materials. For example, the hub can be formed of polycarbonate, and the strain relief can be formed of a relatively less rigid polymer such as polyurethane available under the trade name PELLETHANE.

The strain relief 34 reduces the tendency of the proximal shaft portion 28 to kink just distal of the hub portion 32. The hub portion 32 can be relatively stiff and rigid, whereas the shaft 22 can be relatively flexible, which can create a stress concentration point therebetween, absent the strain relief 34. Thus, the strain relief 34 provides a gradual transition in stiffness between the hub portion 32 and the proximal shaft portion 28. In this particular embodiment, the strain relief 34 has a helical shape and a gradual reduction in profile to provide such a transition in stiffness.

In this particular embodiment, the hub portion 32 includes a single port fluid connector 36 for connection to an ancillary device such as an inflation device (not shown). The hub portion 32 can incorporate more than one connector 36, or no connector at all, depending on the type of intravascular device 20 utilized. For example, an otherwise conventional guide wire may not require a fluid connector 36, whereas an otherwise conventional over-the-wire (OTW) type balloon catheter may require a double port connector 36.

Also in this particular embodiment, the hub assembly 30 includes a pair of wings 38 to facilitate easier handling and manipulation of the device 20. The particular shape of the wings 38 can vary, depending on the manipulation requirements of the device 20. In some instances, wings 38 may not be necessary or desirable.

The hub assembly 30 includes an interference fit member (IFM) 40 connected to a distal portion of the hub 32, proximal of the strain relief 34. The IFM 40 can be connected to any portion of the hub assembly 30, to any portion of the proximal shaft 28, or to any portion of the strain relief 34. The IFM 40 can form an interference fit with any portion the carrier tube 10, such as the inside surface of the carrier tube wall 12 as shown in FIG. 1.

The carrier tube wall 12 and/or the IFM 40 can have sufficient compressibility to deform and thereby permit the IFM 40 to enter into the carrier tube lumen 14 despite a nominal difference in size. The interference fit between the IFM 40 and the carrier tube 10 establishes sufficient friction to resist gravitational and handling forces that can otherwise cause the device 20 to fall out of the carrier tube 10. The friction created by the interference fit can also be sufficiently small to permit easy removal of the device 20 from the carrier tube 10 as shown in FIG. 2.

The IFM 40 can be sized and shaped to be fully or partially disposed inside the carrier tube lumen 14. By extending the IFM 40 into the carrier tube lumen 14 a distance from the proximal end of the carrier tube 10, the IFM 40 is less likely to be accidentally dislodged by rough handling or the like. To this end, the IFM 40 can establish a contact surface area with the inside surface of the carrier tube wall 14 that is distal of the proximal end of the carrier tube 10.

In the embodiment illustrated in FIGS. 1 and 2, the IFM 40 includes a ring having middle portion 42 and end portions 44. End portions 44 can be tapered and can have a diameter or profile that is less than the diameter or profile of the middle portion 42. The middle portion 42 can have a diameter or profile that is greater than the inside diameter or inside profile of the carrier tube 10 adjacent the proximal end thereof.

To illustrate, the middle portion 42 can have a diameter or profile that is about 0.0005 to about 0.010 inches (about 0.013 to about 0.25 millimeters) greater than the inside diameter or inside profile of the carrier tube 10. If the inside diameter of the carrier tube 10 is about 0.17 to about 0.18 inches (about 4.3 to about 4.6 millimeters), the middle portion 42 can have a diameter of about 0.181 to about 0.187 inches (about 4.60 to about 4.75 millimeters).

The remaining Figures described herein illustrate variations of the hub assembly 30 and IFM 40. Except as described and evident from the drawings, the principles of design, function, use and manufacture may be the same as described previously. To this end, similar elements may be numbered the same or have the same last two digits.

Refer now to FIG. 3 which illustrates a partially cross-sectioned exploded view of the proximal portion of the carrier tube 10 and an alternative catheter 120. The catheter 120 includes a hub assembly 130 having a hub 132 and a snap-fit strain relief 134. The snap-fit strain relief 134 can be connected to the hub 132 utilizing a mechanical lock 150. Mechanical lock 150 includes mating parts 152/154 which permit the strain relief 134 to be easily snap-fit onto the hub 132 to establish a rigid connection therebetween, as described by Holman et al.

Figure 4:
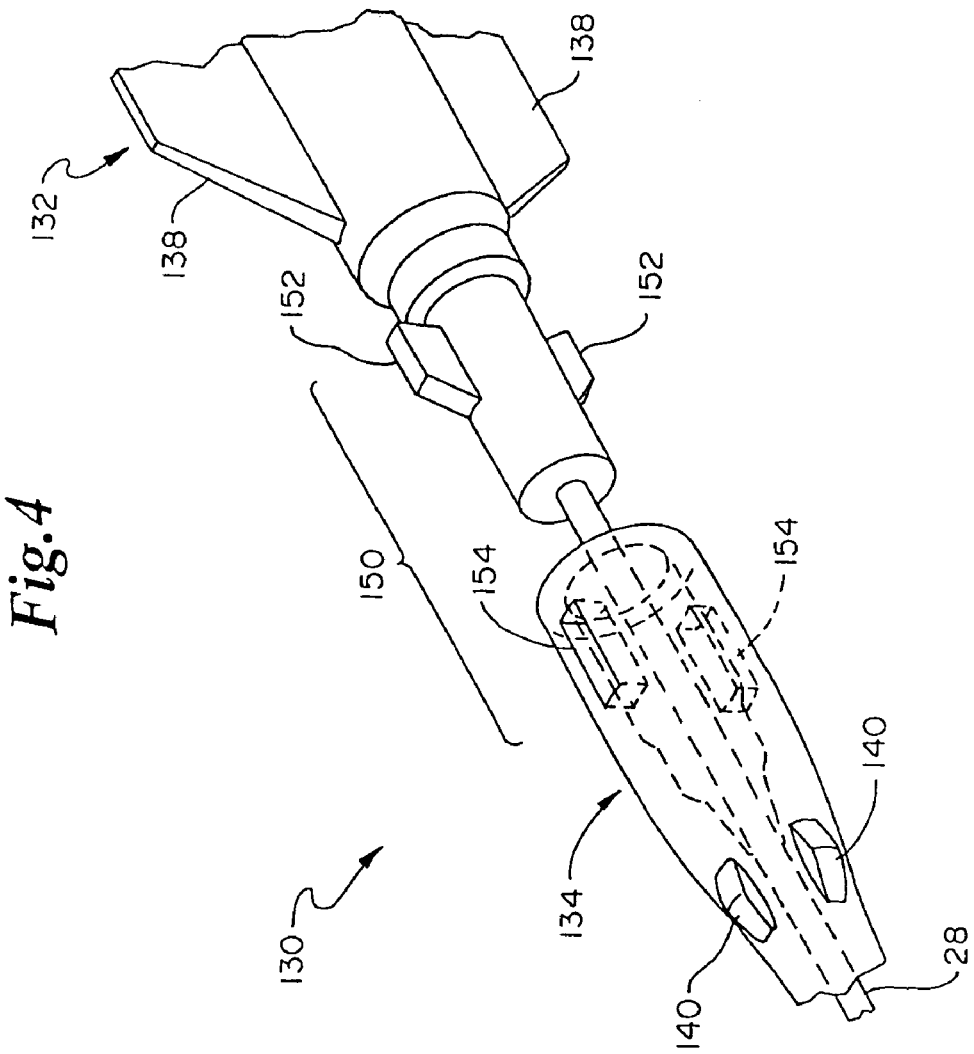
FIG. 4 is an exploded isometric view of the hub assembly illustrated in FIG. 3.

An IFM 140 is disposed on the strain relief 134. The IFM 140 can include a circular ring as shown in FIG. 2 or a plurality of protrusions distributed about the circumference of the strain relief 134 as illustrated in FIG. 4. The IFM 140 includes a middle portion 142 and tapered end portions 144. Middle portion 142 establishes an interference fit with the inside surface of the carrier tube wall 12.

Refer now to FIG. 5 which illustrates a partially cross-sectioned exploded view of the proximal portion of the carrier tube 10 and an alternative catheter 220 disposed therein. The catheter 220 includes a hub assembly 230 having a hub 232 and a snap-fit strain relief 234. The strain relief 234 can be connected to the hub 232 by a mechanical lock. The hub 232 also includes a plurality of grip protrusions 233 disposed about the circumference of the hub 232 proximal of the strain relief 234 and distal of the wings 238 as best seen in FIG. 6. Grip protrusions 233 enhance the ability of the physician to grip the hub assembly 230 to manipulate the catheter 220.

An IFM 240 is disposed on the strain relief 234. The IFM 240 can have a circular ring as illustrated in FIG. 2 or a plurality of protrusions distributed about the circumference of the strain relief 234 as shown in FIG. 6. The IFM 240 includes a middle portion 242 and tapered end portions 244. The middle portion 242 forms an interference fit with the inside surface of the carrier tube wall 12.

Refer now to FIG. 7 which illustrates a plan view of a proximal portion of an alternative catheter 320. The catheter 320 includes a hub assembly 330 having a hub 332 and an integral strain relief 334. An IFM 340 is disposed on the hub 332 just proximal of the strain relief 334. The IFM 340 comprises a thin ring having a middle portion 342 and a tapered proximal portion 344. The middle portion 342 engages the inside surface of the carrier tube wall 12 (not shown) to form an interference fit therebetween.

Refer now to FIG. 8 which illustrates a plan view of a proximal portion of an alternative catheter 420. The catheter 420 includes a hub assembly 430 having a hub 432 and a snap-fit strain relief 434. A mechanical lock 450 having mating members 452/454 mechanically connects the hub 432 to the strain relief 434. An IFM 440 is disposed on a proximal portion of the strain relief 434. The IFM 440 includes a circular ring having a middle portion 442 and a proximal tapered portion 444. The middle portion 442 of the IFM 440 engages the inside surface of the carrier tube wall 12 (not shown) to form an interference fit therebetween.

Refer now to FIG. 9 which illustrates an exploded view of the proximal portion of the carrier tube 10 and an alternative catheter 520 disposed therein. Catheter 520 includes a hub assembly 530 having a hub 532 and a snap-fit strain relief 534. The hub 532 can be connected to the strain relief 534 by a mechanical connection 550 having mating elements 552/554.

An IFM 540 is connected to the strain relief 534 distal of the mechanical connection 550. The IFM 540 includes a pair of opposing flexure arms 542 each having one or more teeth 544. The flexure arms 542 can bias the teeth 544 against the outside surface of the carrier tube wall 12. The teeth 544 form an interference fit with the outside surface of the carrier tube wall 12.

Refer now to FIG. 10 which illustrates a plan view of the proximal portion of the carrier tube 10 and an alternative catheter 620 disposed therein. The catheter 620 includes a hub assembly 630 having a hub 632 and an integral strain relief 634. An IFM 640 is disposed on the hub 632 proximal of the strain relief 634. The IFM 640 includes a pair of opposing flexure arms 642, each having one or more teeth 644. Flexure arms 642 bias the teeth 644 against the outside surface of the carrier tube wall 12 to establish an interference fit therebetween.

Refer now to FIGS. 11-15 which illustrate isometric views of the proximal portion of the carrier tube 10 and alternative designs of a catheter 720 having a double port hub assembly 730. The double port hub assembly 730 is particularly suitable for over the wire (OTW) type balloon catheters. The hub assembly 730 includes a pair of port connectors 736.

In each of the embodiments illustrated in FIGS. 11-15, the hub assembly 730 includes a hub portion 732 and a strain relief portion 734. Also in each of the embodiments illustrated in FIGS. 11-15, an IFM 740 in the form of a plurality of protrusions is disposed on a portion of the hub assembly 730. Each of the protrusions 740 includes a middle portion 742 and tapered end portions 744. The middle portion 742 forms an interference fit with the inside surface of the carrier tube wall 12.

Figure 11:
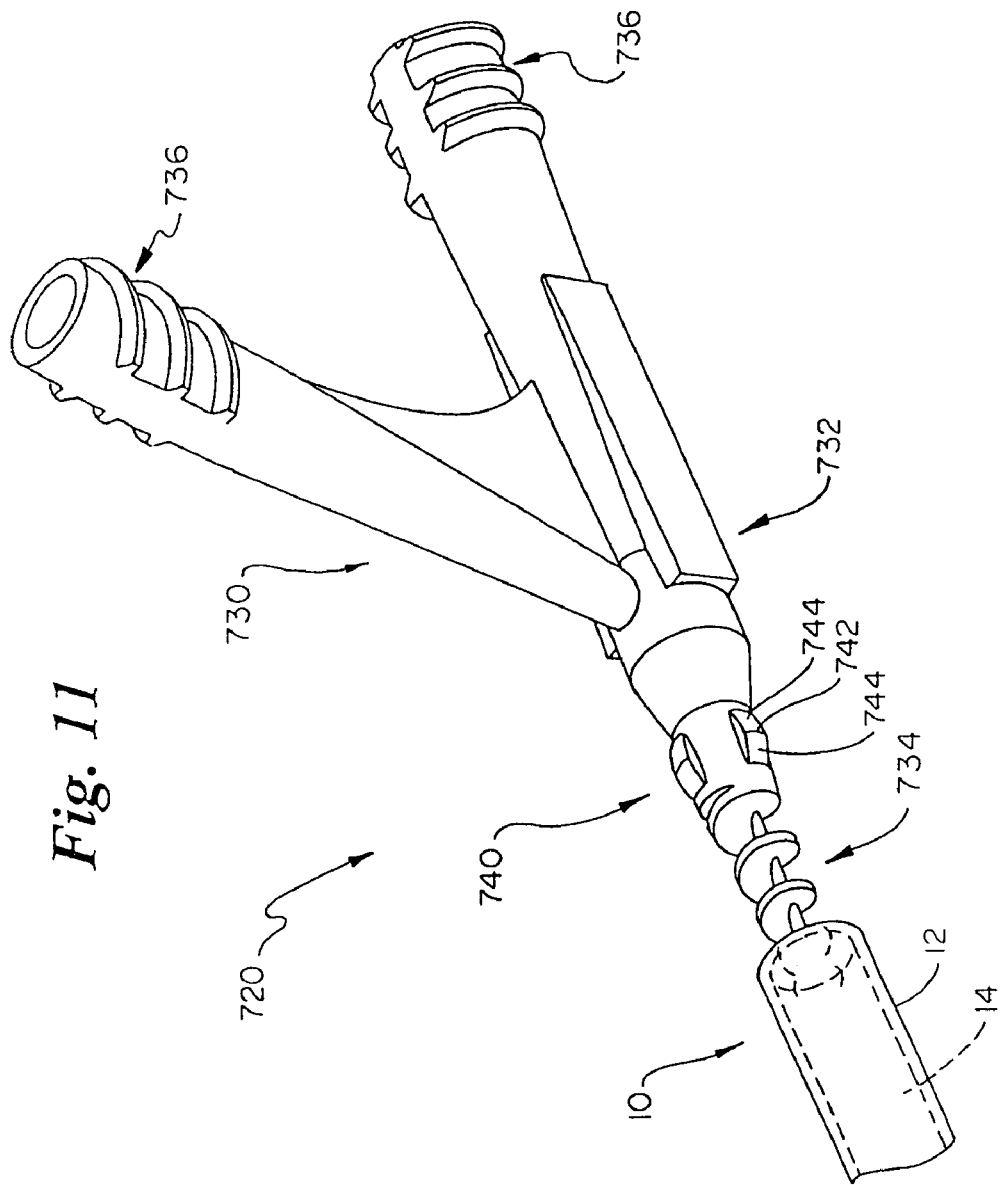
FIG. 11 is an isometric view of a proximal portion of a carrier tube and alternative catheter design, with an IFM disposed on a double port hub assembly.
Figure 12:
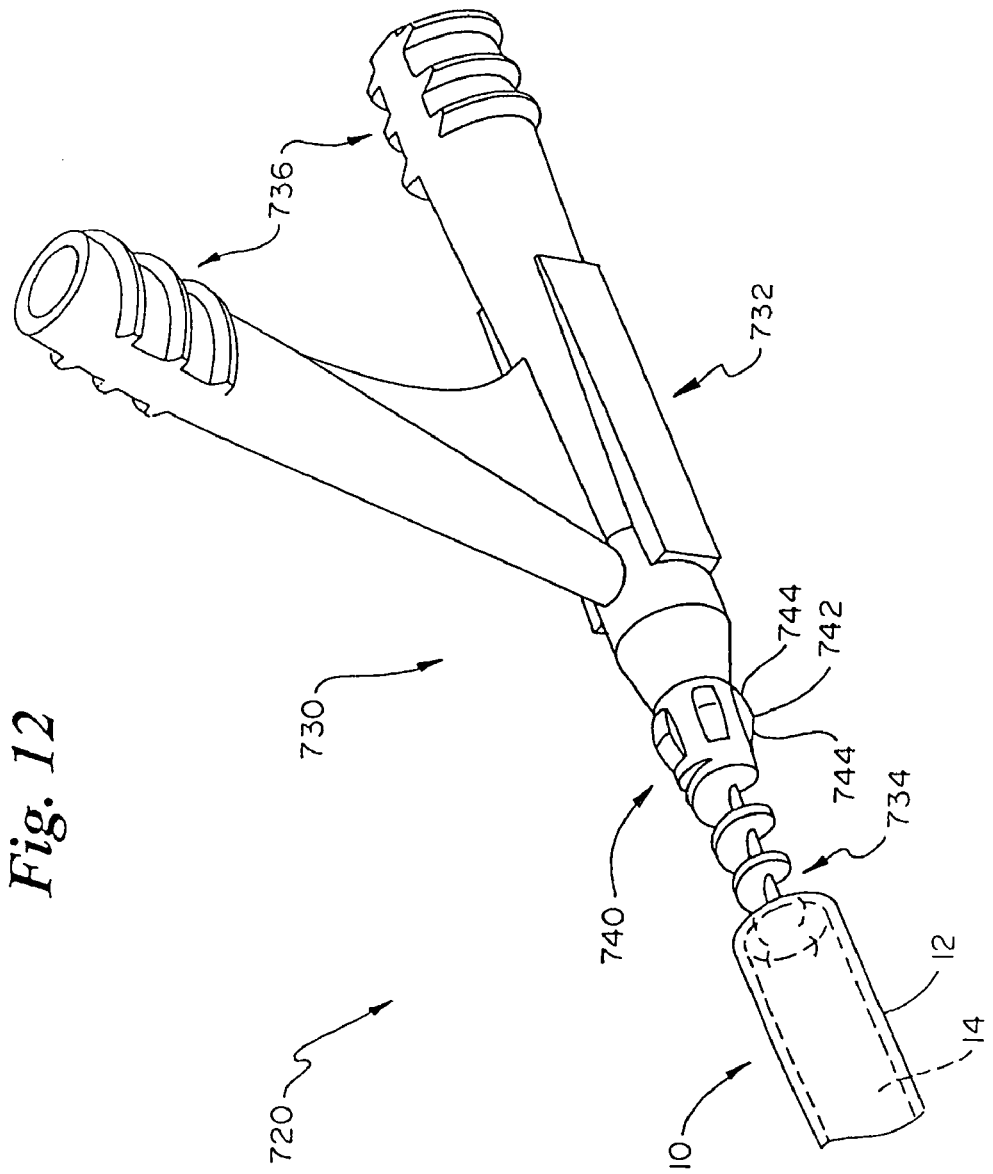
FIG. 12 is an isometric view of a proximal portion of a carrier tube and another alternate catheter design, with an IFM disposed on a double port hub assembly.

In the embodiments illustrated in FIGS. 11 and 12, the hub 732 and the strain relief 734 are integrally formed. In the embodiments illustrated in FIGS. 13-15, the hub 732 and the strain relief 734 include a two-piece construction that may be snap-fit together using a mechanical connection 750 including mating members 752 and 754.

Figure 15:
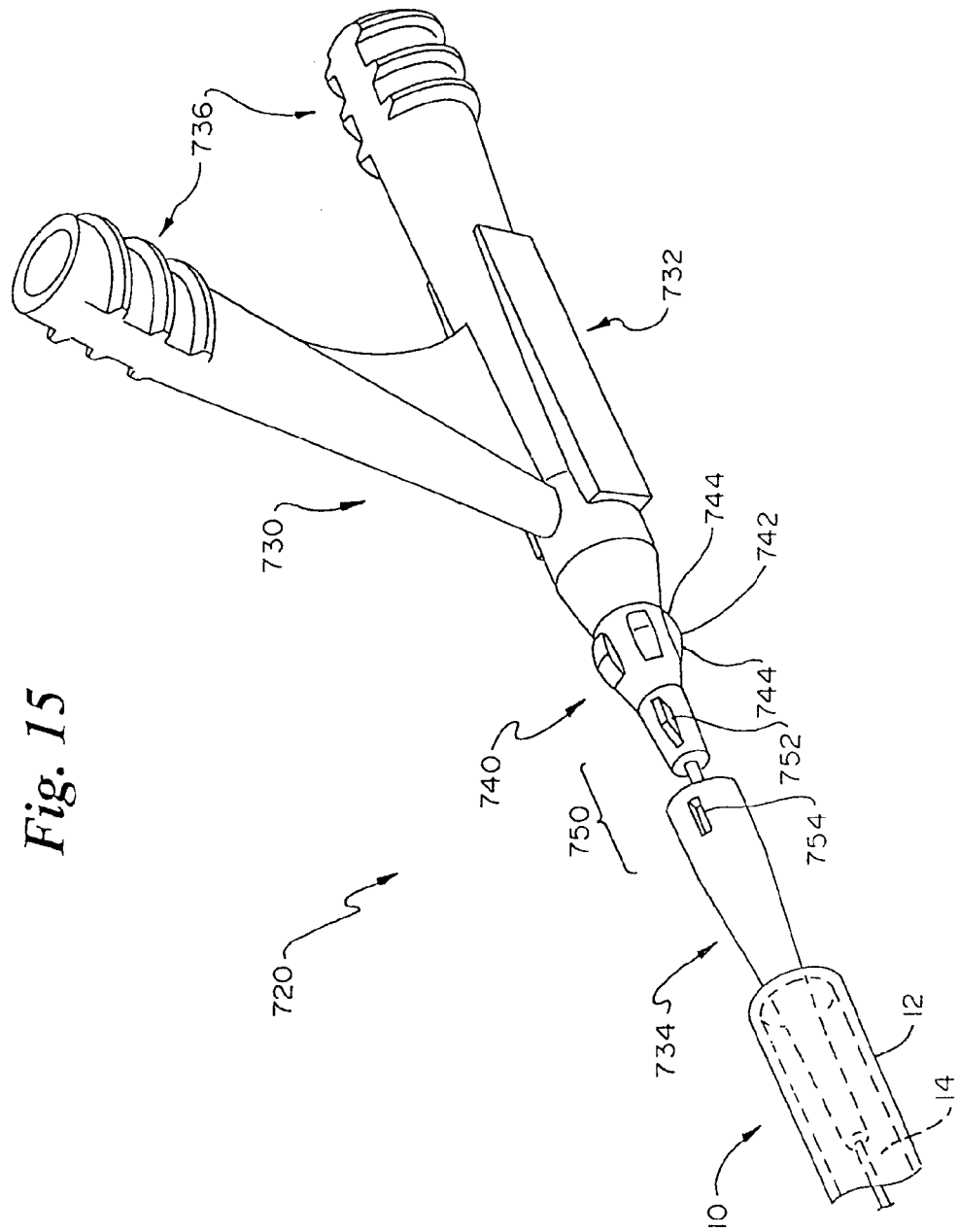
FIG. 15 is an exploded isometric view of a proximal portion of a carrier tube and an alternative catheter design. The catheter has a snap-fit strain relief and has an IFM disposed on a double port hub assembly.

In the embodiments described in FIGS. 11, 12 and 15, the IFM 740 is disposed on a distal portion of the hub 732. In the embodiments illustrated in FIGS. 13 and 14, the IFM 740 is disposed on the strain relief 734.

Figure 13:
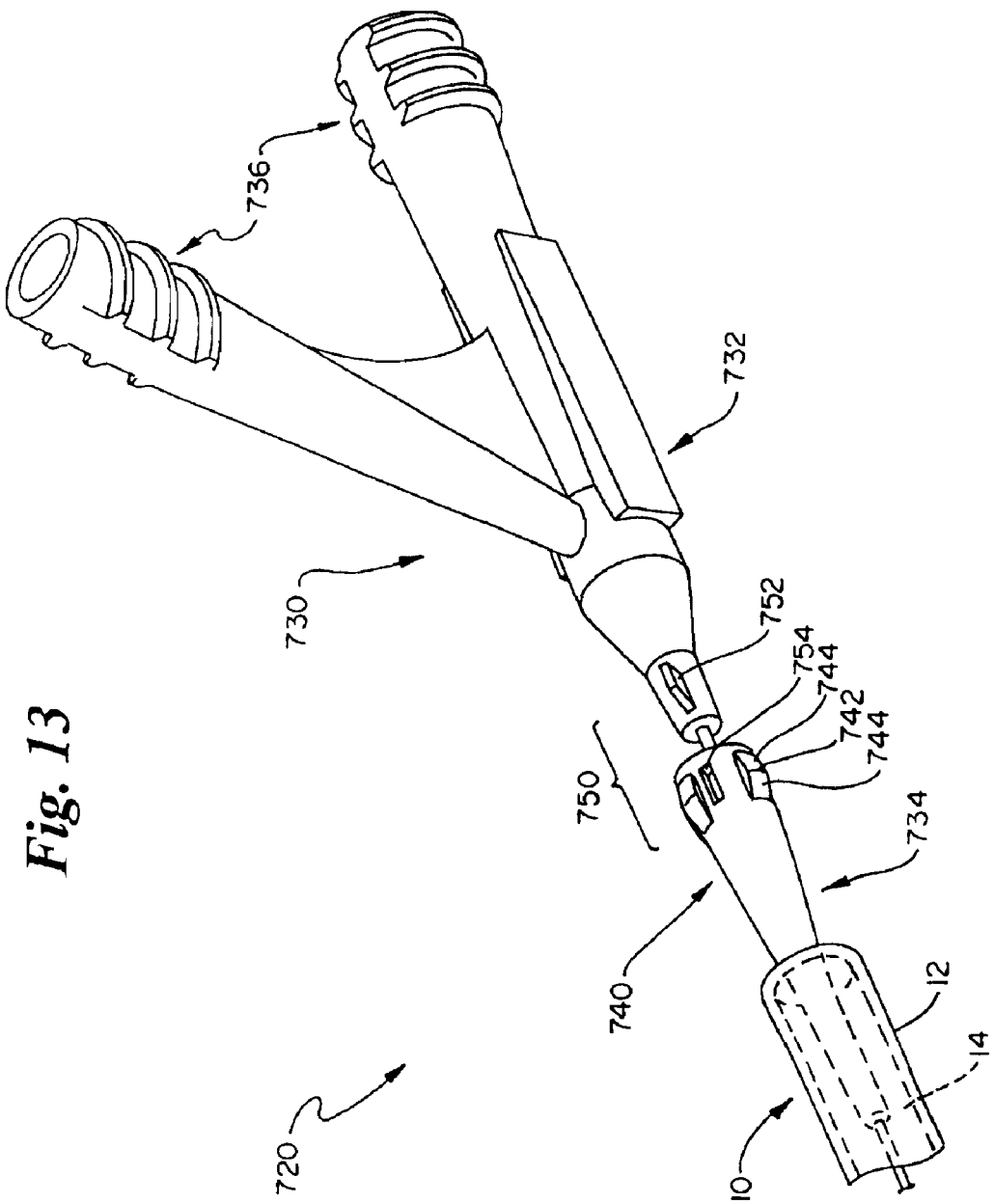
FIG. 13 is an isometric view of a proximal portion of a carrier tube and alternative catheter design. The catheter has a snap-fit strain relief and has an IFM disposed on a double port hub assembly.
Figure 14:
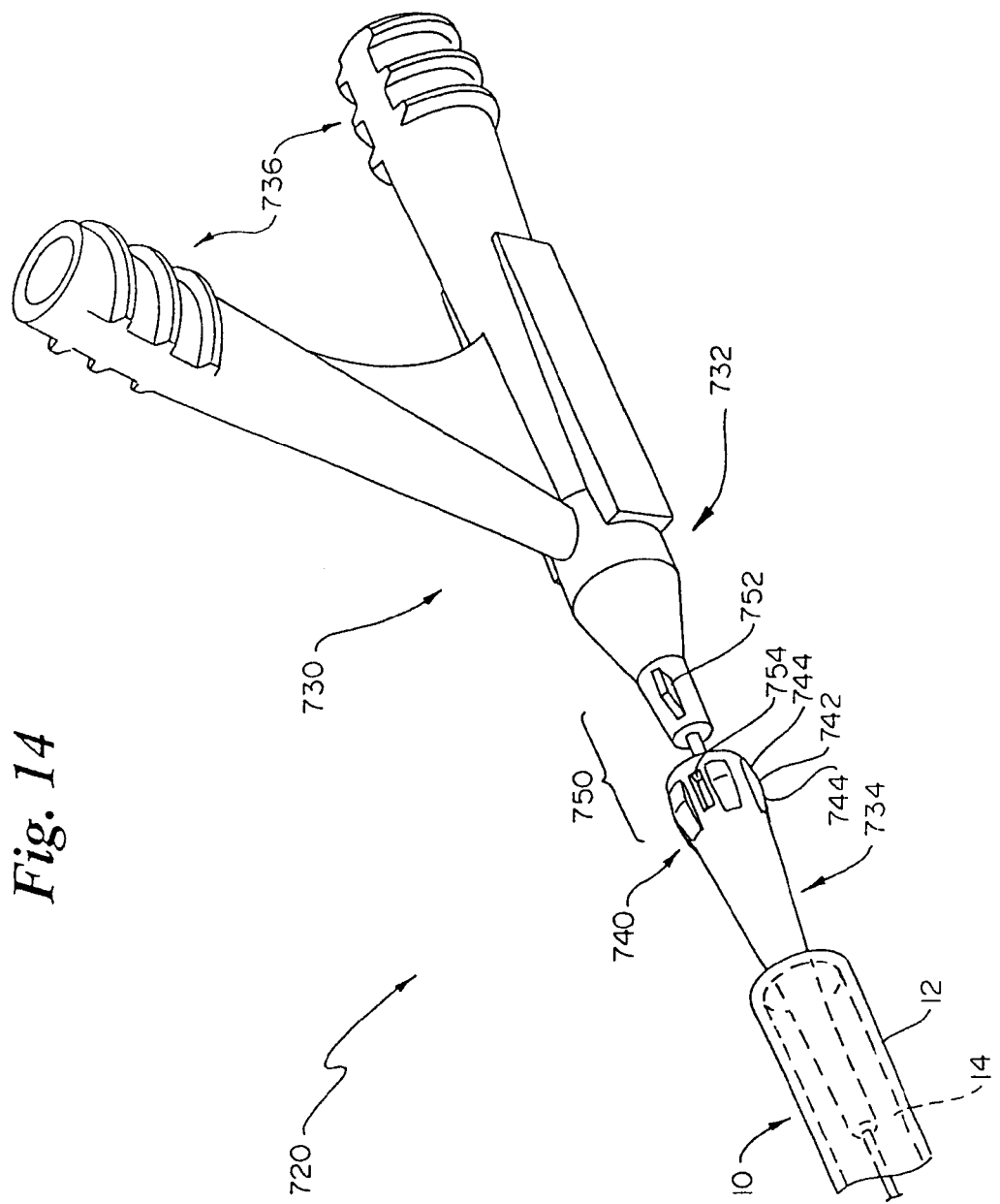
FIG. 14 is an exploded isometric view of view of a proximal portion of a carrier tube and an alternative catheter design. The catheter has a snap-fit strain relief and has an IFM disposed on a double port hub assembly.

In the embodiments illustrated in FIGS. 11 and 13, the IFM 740 has four protrusions distributed about the circumference of hub assembly 730 spaced apart by approximately 90 degrees. In the embodiments illustrated in FIGS. 12, 14 and 15, the IFM 740 has six protrusions spaced approximately 60 degrees apart about the circumference of the hub assembly 730.

FIGS. 16-29 show additional embodiments of releasably connecting or retaining packaging, for example a carrier tube, onto a medical device. The general structure of the medical devices, such as the intravascular devices, and the general structure of the hub assemblies on these devices can be generally similar to those described above.

Figure 16:
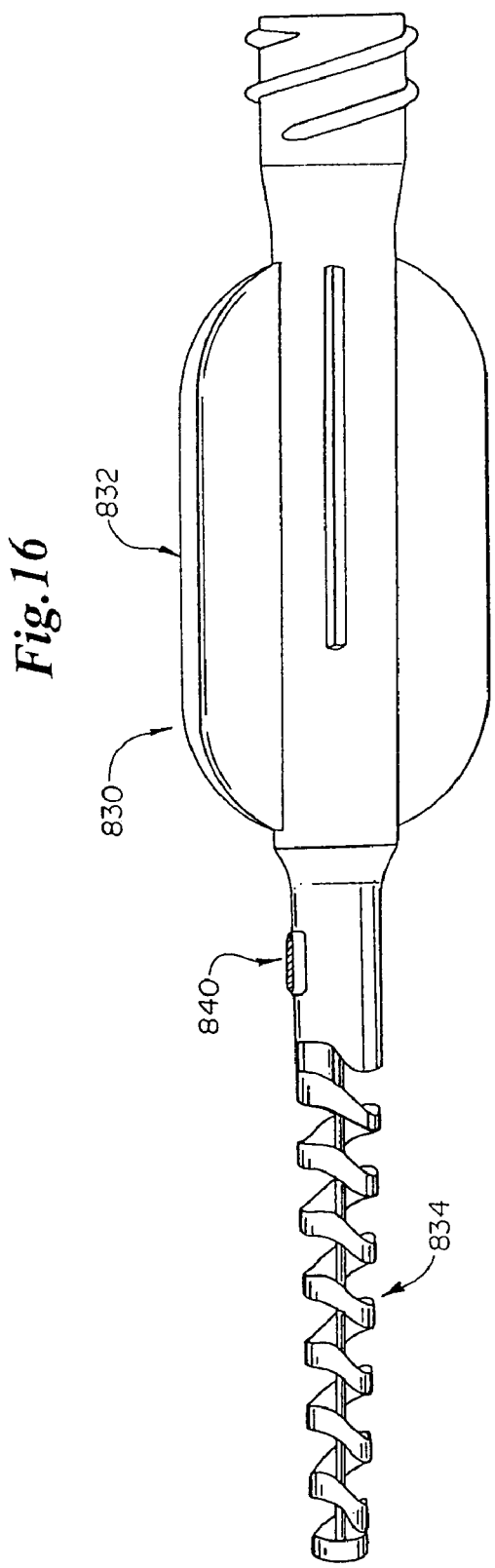
FIG. 16 is a side view of a hub assembly and integral strain relief having a single protrusion.

FIG. 16 is a side view of an embodiment of a hub assembly 830 including a hub portion 832 and a strain relief 834. The hub assembly includes an IFM 840 that has a single protrusion on the hub assembly 830. As shown, the IFM 840 can have a single protrusion disposed on a distal portion of the hub 832, proximal of the strain relief 834. The single protrusion IFM 840 can be connected to any portion of the hub assembly 830, or to any portion of the proximal shaft of a medical device to which the hub assembly 830 is attached. The IFM 840 can form an interference fit with any portion of a package such as a carrier tube. The IFM 840 can form an interference fit with the inside surface of the carrier tube wall.

The interference fit between the IFM 840 and the carrier tube establishes sufficient friction to resist gravitational and handling forces which may otherwise cause the device to fall out of the carrier tube. The friction created by the interference fit may also be sufficiently small to permit easy removal of the device from the carrier tube. As illustrated, the IFM 840 has a single protrusion.

FIG. 17 is a partial side view of another embodiment of a hub assembly 830 including a hub portion 832 and a strain relief 834. The hub assembly 830 includes an IFM portion 840 that has one or more portions that are generally non-circular in cross-sectional shape. For example, the embodiment of FIG. 17 includes two non-circular portions 841 and 843 (in cross section) that are disposed at offset positions relative to one another by a degree of rotation about the longitudinal axis of the hub assembly 830.

FIGS. 18 and 19 are cross sectional views taken along lines 18-18 and 19-19 respectively, of FIG. 17, to better illustrate the generally non-circular shape of the outer surface of the portions 841 and 843. The non-circular portions 841 and 843 can be disposed at positions that are offset from one another by more than about zero degrees but less than about 180 degrees. In particular, the non-circular portions 841 and 843 can be offset from one another by about 30 to about 120 degrees and in particular can be offset by about 90 degrees.

In other embodiments, there can be only one, or can be more than two generally non-circular portions. The generally non-circular shape of the IFM portion 840 can form an interference fit with any portion of a package such as a carrier tube. The IFM portion 840 can form an interference fit with an inside surface of a carrier tube wall.

The interference fit between the IFM portion 840 and the carrier tube establishes sufficient friction to resist gravitational and handling forces which may otherwise cause the device to fall out of the carrier tube. The friction created by the interference fit may also be sufficiently small to permit easy removal of the device from the carrier tube.

FIGS. 20-24 show another alternative embodiment of releasably connecting and maintaining packaging on an intravascular device. In this embodiment, a separate interference structure 873 is used to mate with the packaging and the intravascular device.

FIG. 20 is a perspective view of a hub assembly 830 including a hub portion 832 and a strain relief 834. The hub assembly 830 includes one or more grooves 860 therein. The embodiment shown shows a single groove 860 in a distal portion of the hub 832, proximal of the strain relief 834. In another embodiment, the groove 860 can be defined in any portion of the hub assembly 830, or in any portion of the proximal shaft of the medical device onto which the hub assembly is mounted. The groove 860 can extend annularly around the entire circumference of the assembly 830, as shown, or can be defined in only a portion of the circumference of the assembly 830.

FIG. 21 is a perspective view of a package 810, such as a carrier tube, that includes a package wall 812 defining an elongate package lumen 814 therein. One or more openings 865 are defined in the package wall 812. In the embodiment shown, two openings 865 are defined in the package wall 812 adjacent a proximal end 871 of the package 810. In other embodiments, there can be only one opening, or can be more than two openings, and the openings can be in other locations along the longitudinal axis of the packaging.

Figure 23:
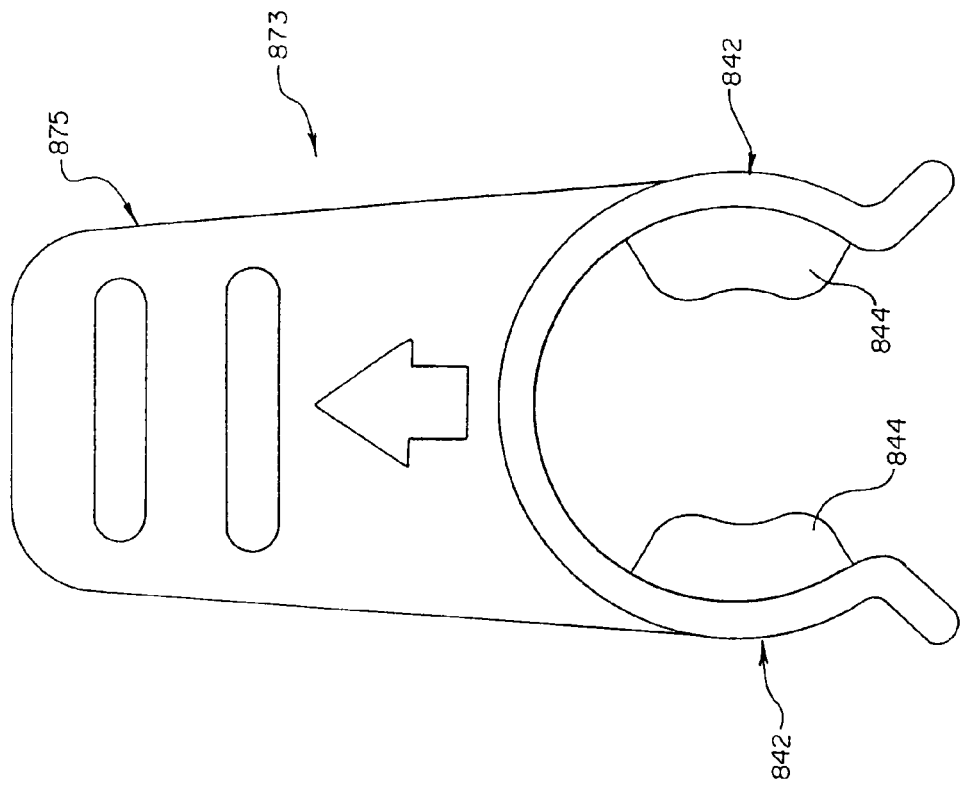
FIG. 23 is a side view of the interference structure of FIG. 22.
Figure 22:
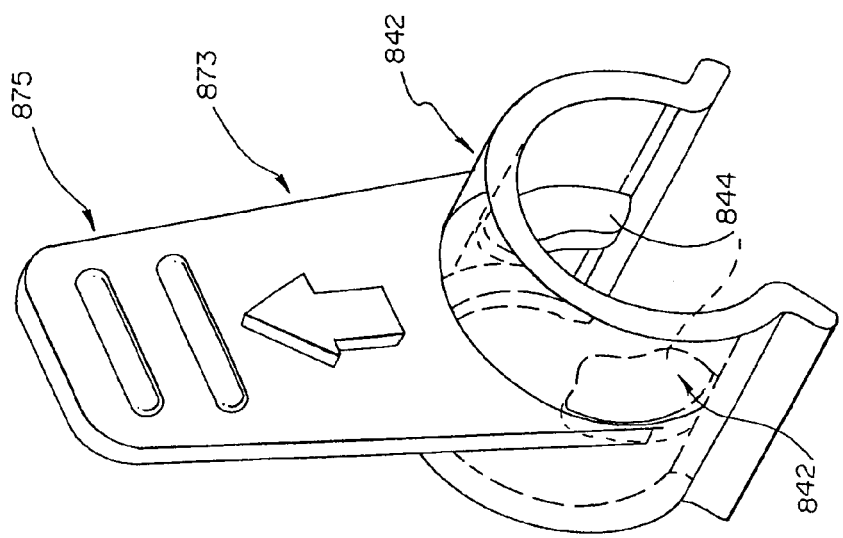
FIG. 22 is a perspective view of an interference structure adapted to cooperate with the hub assembly of FIG. 20 and the carrier tube of FIG. 21.

FIG. 22 is a perspective view of an interference structure 873 and FIG. 23 is a side view of the interference structure 873. The interference structure 873 includes structure that is adapted and configured to mate with one or more of the grooves 860 in the hub assembly 830, as described above with reference to FIG. 20, and one or more of the openings 865 defined in the package wall 812, as described above with reference to FIG. 21, to releasably connect and maintain the package 810 on an intravascular device.

In the embodiment shown, the interference structure 873 is a clip, such as a spring clip. The clip 873 includes a handle portion B875 and a pair of opposing flexure arms 842, each having one or more teeth 844 adapted and configured to mate with and extend through the one or more openings 865 defined in the package wall 812, and mate with and extend into the one or more grooves 860 in the hub assembly 830 to releasably connect and maintain the package 810 on an intravascular device. Flexure arms 842 bias the teeth 844 through the openings 865 and into the groove 860 to establish an interference fit.

FIG. 24 is a perspective view of the clip 873 mounted onto the package 810 and the hub assembly 830. The teeth 844 on the clip 873 mate with and extend through the openings 865 defined in the package wall 812, and mate with and extend into the groove 860 in the hub assembly 830 to releasably connect and maintain the package 810 on an intravascular device to which the hub assembly is mounted. Flexure arms 842 bias the teeth 844 through the openings 865 and into the groove 860 to establish an interference fit. The interference fit created by the clip establishes sufficient friction to resist gravitational and handling forces which may otherwise cause the device to fall out of the package. The friction created by the interference fit may also be sufficiently small to permit easy removal of the clip, and therefore permit easy removal of the device from the package.

Figure 26:
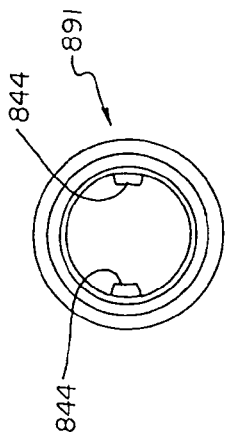
FIG. 26 is a view down the longitudinal axis of the connector structure of FIG. 25.
Figure 27:
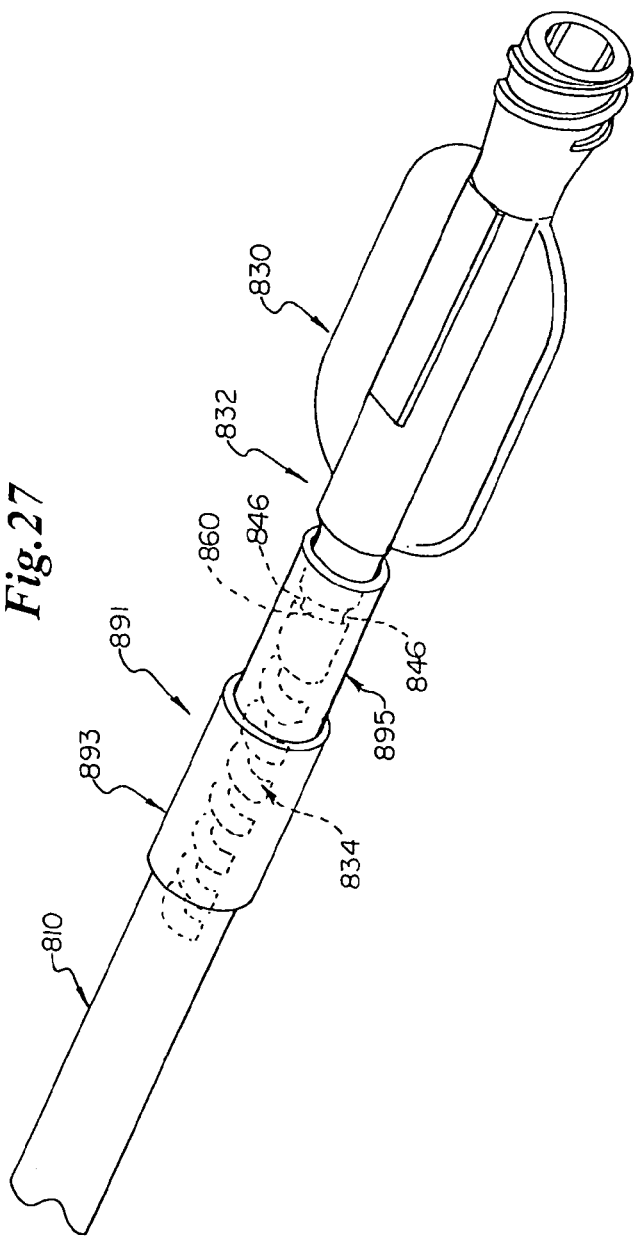
FIG. 27 is a perspective view of a hub assembly and package joined with the connector structure of FIG. 26.

FIGS. 25-27 show another alternative embodiment of structure and methods of releasably connecting and maintaining packaging on an intravascular device. In this embodiment, a separate connector structure 891 is used to mate with the packaging and the intravascular device.

FIG. 25 is a perspective view of a connector structure and FIG. 26 is a view down the longitudinal axis of the connector structure 891. The connector structure 891 is adapted and configured to mate with the package and with structure on an intravascular device to releasably connect the packaging to the intravascular device. In the embodiment shown, the connector 891 includes a package mating portion 893 and a hub assembly mating portion 895. The package mating portion 893 is a generally tubular structure defining an inner lumen 894. The inner lumen 894 is sized such that an end of a packaging can be inserted therein, and form an interference fit between the outer surface of the packaging, and the inner surface of the lumen 894.

The hub assembly mating portion 895 is a generally tubular structure defining a wall 885 and an inner lumen 887. The inner lumen 887 can be sized and configured to mate with the hub assembly 830. In the embodiment shown, a wall 885 includes a pair of opposing protrusions 846 adapted and configured to mate with structure on the hub assembly 830 to releasably connect and maintain the connector on the hub assembly 830.

FIG. 27 is a perspective view of the hub assembly 830, the package 810, and the connector structure 891 and demonstrates a method of using the connector structure 891 to releasably connect the hub assembly 830 and the package 810. The hub assembly 830 includes a hub portion 832 and a strain relief 834. The hub assembly 830 includes one or more grooves 860 therein, and can include the same general structure as discussed above with reference to FIG. 21.

The hub assembly 830 is inserted into and mates with the hub assembly mating portion 895 of the connector structure 891. The protrusions 846 of the connector structure 891 mate with and extend into the groove 860 to releasably connect and maintain the connector structure 891 on the hub assembly 830. The interference fit created by the protrusions 846 and groove or grooves 860 establishes sufficient friction to resist gravitational and handling forces. The friction created by the interference fit may also be sufficiently small to permit easy removal of the connector structure 891.

The package 810 is inserted over a portion of the strain relief 834, and into the inner lumen 894 of the package mating portion 893. The package 810 and the inner lumen 894 are sized such that an interference fit is created between the outer surface of the package 810, and the inner surface of the lumen 894. The package wall 812 and/or the package mating portion 893 has sufficient stretch, and or compressibility to deform and thereby permit the package 810 to enter into the lumen 894 of the package mating portion 893 despite nominal difference in size. The interference fit created establishes sufficient friction to resist gravitational and handling forces. The friction created by the interference fit may also be sufficiently small to permit easy removal of the package 810 from the connector structure 891.

Figure 28:
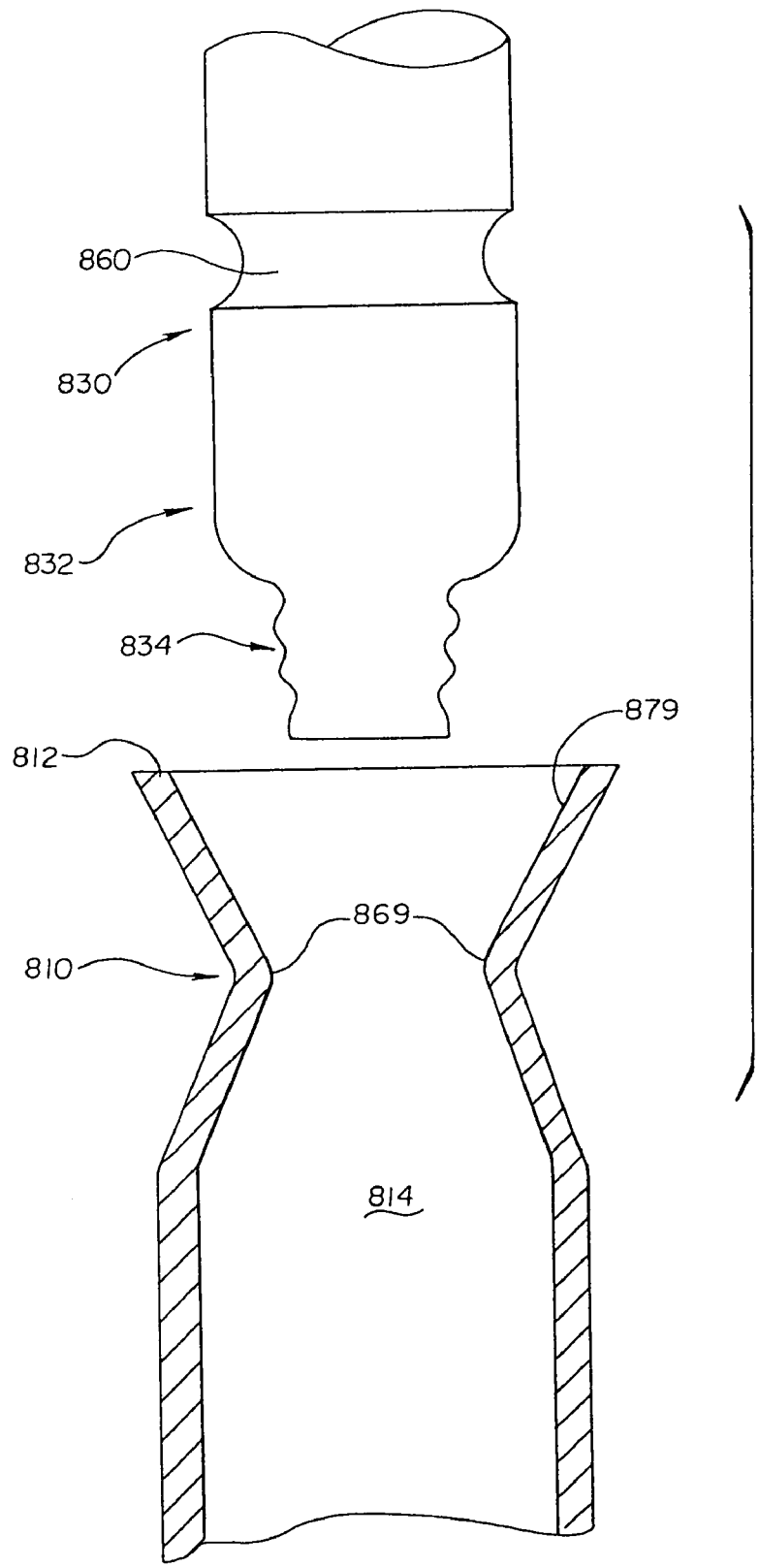
FIG. 28 is a partial perspective view of a hub assembly.

FIG. 28 shows another alternative embodiment of structure and methods of releasably connecting and maintaining packaging on an intravascular device. FIG. 28 is a partial perspective view of a hub assembly 830 including a hub portion 832 and a strain relief 834, and a package 810. The hub assembly 830 includes one or more grooves 860 therein. The embodiment shown shows a single groove 860 in a distal portion of the hub 832, proximal of the strain relief 834. In another embodiment, the groove 860 can be defined in any portion of the hub assembly 830, or in any portion of the proximal shaft of the medical device onto which the hub assembly is mounted. The groove 860 can extend annularly around the entire circumference of the assembly 830, as shown, or can be defined in only a portion of the circumference of the assembly 830.

The package 810, such as a carrier tube, includes a package wall 812 defining an elongate package lumen 814 therein. The lumen 814 includes at least one reduced diameter portion 869 and a flared end portion 879. To connect the package 810 to the hub assembly 830, a portion of the hub assembly 830 can be inserted into the lumen 814, and the reduced diameter portion 869 of the package 810 can mate with the groove 860 to releasably connect and maintain the package 810 on the hub assembly 830. The reduced diameter portion 869 of the package wall 812 has sufficient stretch and/or compressibility to deform and thereby permit the hub assembly 830 to enter into the lumen 814 despite a nominal difference in size. The interference fit created establishes sufficient friction to resist gravitational and handling forces. The friction created by the interference fit may also be sufficiently small to permit easy removal of the package 810 from the hub assembly 830.

Figure 29:
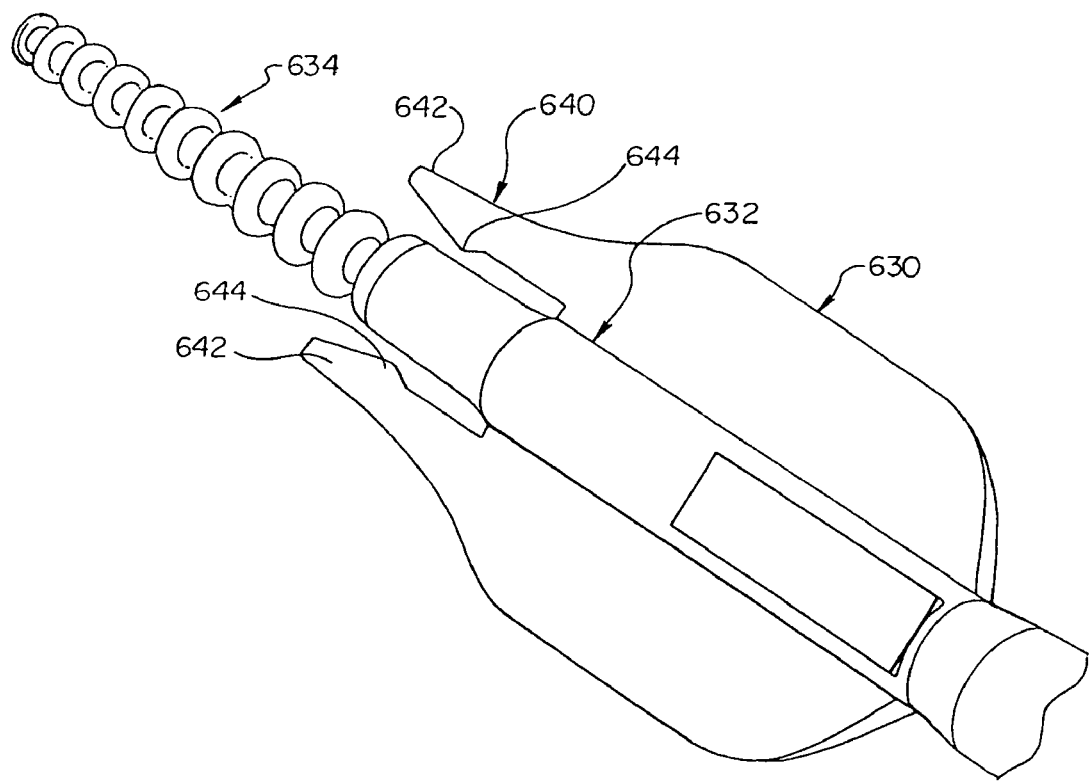
FIG. 29 is a perspective view of a hub assembly similar to the embodiment of FIG. 10.

FIG. 29 illustrates a perspective view of embodiment of a hub assembly 630 similar to the embodiment of FIG. 10, wherein like reference numerals indicate like structure. The hub assembly 630 has a hub 632 and an integral strain relief 634. An IFM 640 is disposed on the hub 632 proximal of the strain relief 634. The IFM 640 includes a pair of opposing flexure arms 642, each having one or more teeth 644. Flexure arms 642 bias the teeth 644 against the outside surface of the carrier tube wall to establish an interference fit therebetween. The embodiment shown in FIG. 29 has a slightly different structure for the flexure arms 642 and teeth 644.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A medical assembly comprising:
 a package having a package lumen defined by a package lumen wall;
 an intravascular device comprising an elongate shaft having a proximal portion and a distal portion;
 a hub assembly connected to the proximal portion of the elongate shaft, such that the hub assembly is in a fixed longitudinal position relative to the shaft; and
 an interference fit member (IFM) affixed to the hub assembly such that the IFM is in a fixed longitudinal position relative to the shaft, the IFM comprising one or more protrusions extending from a sidewall of the hub assembly, the one or more protrusions are distributed around a circumference of the sidewall of the hub assembly and each protrusion includes an elevated middle portion and tapered end portions, the one or more protrusions being adapted and configured to form an interference fit with the package lumen wall when the IFM is disposed in the package lumen, wherein the package encloses the distal portion of the elongate shaft when the one or more protrusions are interference fit with the package lumen wall.

2. The medical assembly of claim 1, wherein the interference fit establishes sufficient friction to resist gravitational and handling forces which may otherwise cause the IFM to fall out of the package lumen.

3. The medical assembly of claim 2, wherein the friction created by the interference fit is sufficiently small to permit easy removal of the IFM from the package lumen.

4. The medical assembly of claim 1, wherein the IFM is configured to be fully disposed in the package lumen.

5. The medical assembly of claim 1, wherein the IFM is configured to form an interference fit with an inside surface of the package lumen wall.

6. The medical assembly of claim 1, wherein the IFM has an outside diameter greater than an inside diameter of the package lumen wall.

7. The medical assembly of claim 1, wherein the IFM has an outside cross-sectional dimension greater than an inside cross-sectional dimension of the package lumen wall.

8. The medical assembly of claim 1, wherein the IFM is formed as an integral portion of the hub assembly.

9. The medical assembly of claim 1, wherein the hub assembly comprises a hub and a strain relief, and wherein the IFM is carried by the hub.

10. The medical assembly of claim 1, wherein the hub assembly comprises a hub and a strain relief, and wherein the IFM is carried by the strain relief.

11. The medical assembly of claim 1, wherein the hub assembly comprises a hub and a strain relief, and wherein the hub and the strain relief are integrally formed.

12. The medical assembly of claim 1, wherein the hub assembly comprises a hub and a strain relief, and wherein the hub and the strain relief are connected.

13. The medical assembly of claim 12, wherein the connection between the hub and the strain relief comprises a bond.

14. The medical assembly of claim 1, wherein the IFM comprises an interference structure that is formed independently of the hub assembly and wherein the IFM is configured to provide an interference fit with the package lumen wall and with the hub assembly.

15. The medical assembly of claim 1, wherein the IFM comprises a single protrusion.

16. The medical assembly of claim 1, wherein the IFM comprises 4 protrusions.

17. The medical assembly of claim 1, wherein the IFM comprises 6 protrusions.

18. The medical assembly of claim 1, wherein the protrusions are disposed at even intervals around the circumference.

19. The medical assembly of claim 1, wherein the hub assembly comprises a hub and a strain relief.

* * * * *

UNITED STATES PATENT AND TRADEMARK OFFICE
CERTIFICATE OF CORRECTION

PATENT NO. : 7,625,365 B2  Page 1 of 1
APPLICATION NO. : 10/244870
DATED : December 1, 2009
INVENTOR(S) : McGlinch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1291 days.

Signed and Sealed this

Twenty-sixth Day of October, 2010

David J. Kappos
*Director of the United States Patent and Trademark Office*